(12) United States Patent
Shreve et al.

(10) Patent No.: US 8,961,783 B2
(45) Date of Patent: Feb. 24, 2015

(54) APPARATUS AND METHODS FOR PREPARATIVE LIQUID CHROMATOGRAPHY

(75) Inventors: Joshua A. Shreve, Franklin, MA (US); Michael R. Jackson, Woonsocket, RI (US)

(73) Assignee: Waters Technologies Corporation, Milford, MA (US)

( * ) Notice: Subject to any disclaimer, the term of this patent is extended or adjusted under 35 U.S.C. 154(b) by 1116 days.

(21) Appl. No.: 12/555,032

(22) Filed: Sep. 8, 2009

(65) Prior Publication Data

US 2010/0065495 A1 Mar. 18, 2010

Related U.S. Application Data

(60) Provisional application No. 61/096,468, filed on Sep. 12, 2008.

(51) Int. Cl.
*G01N 30/34* (2006.01)
*B01D 15/16* (2006.01)

(52) U.S. Cl.
CPC .............. *G01N 30/34* (2013.01); *B01D 15/166* (2013.01)
USPC ......................... 210/198.2; 210/656; 210/101

(58) Field of Classification Search
CPC .............................. G01N 30/34; B01D 15/166
USPC ................. 210/198.2, 635, 656, 101
See application file for complete search history.

(56) References Cited

U.S. PATENT DOCUMENTS

| | | | | |
|---|---|---|---|---|
| 4,128,476 A * | 12/1978 | Rock | ............................. | 210/659 |
| 4,133,767 A * | 1/1979 | Bakalyar et al. | .............. | 210/659 |
| 4,239,623 A | 12/1980 | Schrenker | | |
| 4,311,586 A * | 1/1982 | Baldwin et al. | ................ | 210/101 |
| 4,448,684 A * | 5/1984 | Paradis | ...................... | 210/198.2 |
| 4,595,496 A * | 6/1986 | Carson | ......................... | 210/101 |
| 4,714,545 A * | 12/1987 | Bente et al. | ................... | 210/101 |
| 4,728,434 A * | 3/1988 | Trafford | ........................ | 210/656 |
| 4,879,029 A * | 11/1989 | Whitehead | ................ | 210/198.2 |
| 4,980,059 A * | 12/1990 | Barlow et al. | .............. | 210/198.2 |
| 5,076,909 A * | 12/1991 | Overfield et al. | .............. | 208/177 |
| 5,080,784 A * | 1/1992 | James et al. | .............. | 210/198.2 |
| 5,089,124 A * | 2/1992 | Mahar et al. | ................ | 210/198.2 |
| 5,862,832 A | 1/1999 | Victor et al. | | |
| 6,099,724 A | 8/2000 | Dourdeville | | |
| 6,497,820 B1 * | 12/2002 | Goetzinger et al. | ............ | 506/15 |
| 6,793,815 B2 * | 9/2004 | Hoffmann | .................. | 210/198.2 |

(Continued)

OTHER PUBLICATIONS

Snyder (Introduction to Modern Liquid Chromatography, 1979, John Wiley & Sons, pp. 88-90.*

*Primary Examiner* — Ernest G Therkorn
(74) *Attorney, Agent, or Firm* — Waters Technologies Corporation

(57) ABSTRACT

A method of liquid chromatography includes providing one or more solvent reservoirs, providing a solvent pump, drawing one or more solvents into the pump in response to a pressure drop that promotes outgassing of the solvents, and dispersing outgassed bubbles into smaller bubbles to promote re-dissolution of the gas. A liquid-chromatography apparatus includes at least two solvent reservoirs, a pump, at least one bubble-dispersing unit that receives a pressurized flow of proportioned solvents from the pump, and a control unit. The control unit includes a processor and a memory that stores instructions; the control unit controls proportioning of solvents to obtain a preselected solvent composition, and pumping at flow rates to support preparative-scale or process-scale liquid chromatography.

12 Claims, 2 Drawing Sheets

(56) References Cited

U.S. PATENT DOCUMENTS

| | | | |
|---|---|---|---|
| 7,229,551 B2* | 6/2007 | Murata et al. | 210/198.2 |
| 7,396,469 B2* | 7/2008 | Andrews et al. | 210/656 |
| 7,550,081 B2* | 6/2009 | Kitagawa | 210/198.2 |
| 7,670,480 B2* | 3/2010 | Witt et al. | 210/101 |
| 7,754,075 B2* | 7/2010 | Richardson et al. | 210/198.2 |
| 2002/0185441 A1* | 12/2002 | Gjerde et al. | 210/656 |
| 2004/0035793 A1* | 2/2004 | Legendre et al. | 210/656 |
| 2004/0108273 A1* | 6/2004 | Richardson et al. | 210/656 |
| 2004/0178133 A1* | 9/2004 | Deguchi et al. | 210/198.2 |
| 2005/0218055 A1* | 10/2005 | Hayashi et al. | 210/198.2 |
| 2005/0224403 A1* | 10/2005 | Allington et al. | 210/198.2 |
| 2006/0201885 A1* | 9/2006 | Davison | 210/656 |
| 2007/0034557 A1* | 2/2007 | Ito | 210/101 |
| 2010/0065495 A1* | 3/2010 | Shreve et al. | 210/635 |

* cited by examiner

APPARATUS AND METHODS FOR PREPARATIVE LIQUID CHROMATOGRAPHY

CROSS-REFERENCE TO RELATED APPLICATION

This application claims priority to and benefit of U.S. Provisional Patent Application Ser. No. 61/096,468, filed Sep. 12, 2008, the contents of which are incorporated herein by reference in their entirety.

TECHNICAL FIELD

The invention generally relates to chromatography, and, more particularly, to apparatus and methods for liquid chromatography at high flow rates.

BACKGROUND INFORMATION

Liquid chromatography is a method for separating individual compounds in a mixture of compounds. Liquid chromatography is often used for sample analysis or for purification of a particular compound in a sample mixture. Typically, a sample containing a number of compounds is injected into a fluid stream (typically a solvent of constant or varying composition,) and directed through a chromatographic column. The column separates the compounds in the sample mixture in response to their differential retention in the column. Concentration peaks associated with the separated compounds typically emerge in sequence from the column. Sample purification typically entails higher solvent flow rates, and larger sample quantities, than sample analysis.

The chromatographic peaks are often characterized with respect to their retention time, that is, the time in which the center of the band transits the detector relative to the time of injection. In many applications, the retention time of a peak is used to infer the identity of the eluting analyte based upon related analyses incorporating standards or calibrants. The presence of the separated species are often distinguished through use of a refractometer or an absorbtometer utilizing ultraviolet (UV) light.

In addition to separation columns and detectors, liquid-chromatography (LC) instruments typically include solvent reservoirs, pumps, filters, check valves, sample-injection valves, and other fluid-handling and analysis components. Typically, mobile-phase solvents are stored in reservoirs, and delivered via reciprocating-cylinder based pumps. Sample materials are often injected via syringe-type pumps. For example, some LC systems inject a sample by aspirating (pulling) a fluid-based sample into a tube via a needle or capillary and then into a sample loop. The sample is then injected from the sample loop into the mobile-phase stream on its way to a separation column.

In many scientific or industrial applications, compounds are purified for testing, for further analysis, or for volume production. For target purification, it is often desirable to recover the target compound with as high a purity as possible, and to separate the largest possible quantity of a sample with each run to reduce labor, run time, and other costs. Thus, it is often desirable to process samples at high flow rates to obtain purified compounds in larger quantities and/or more quickly. It is also commonly desirable to operate at pressures in the range of 1,000-5,000 pounds per square inch (psi) or higher. Such pressures are encountered in high-performance (also known as high-pressure) liquid chromatography (HPLC).

Processing liquids at high flow rates and high pressures, however, can cause problems. Pump-blended solvents often encounter outgassing, either due to pressure drops experienced in the pump head or solubility reduction upon solvent mixing. Outgassing in the pump head can impair mixing, and outgassed bubbles, in general, can impair LC performance by altering the behavior of various components. For example, bubbles passing through an optical detector can alter the spectral behavior of the detector, e.g., by causing spectral spikes.

As noted, bubble production can occur during solvent mixing due lower gas solubility of some solvent mixtures relative to the unmixed solvents (such as water and methanol.) One solution to this problem, at least for isocratic analysis, is to use premixed solvents.

More general solutions to bubble production include helium sparging and vacuum degassing. Often used to degas pre-mixed solvents, helium sparging is particularly effective where the solvent reservoir can be pressurized. Sparging, however, can be costly and inconvenient. In-line vacuum degassers offer an alternative solution. Such degassers utilize a semipermeable membrane disposed in an evacuation chamber that removes dissolved gases. Degassers, however, also add cost, and can be ineffective for high flow rates as often utilized in preparative- and process-scale liquid chromatography.

SUMMARY OF THE INVENTION

The invention arises, in part, from the realization that the impact of bubble formation in preparative- and process-scale LC apparatus can be mitigated by breaking up the bubbles so that the remaining smaller bubbles are more readily dissolved. Preferably, the bubbles are dispersed, i.e., fragmented, via the effect of one or more bubble-dispersing components placed in the liquid pathway between one or more bubble sources, such as pumps or mixers, and one or more detectors. The dissolved gas then has a much smaller effect on detector readings than would bubbles passing through the detector. The invention is particularly well suited to apparatus where sparging and/or vacuum degassing are ineffective and/or too complex and/or too costly to implement. Thus, for example, the invention is particularly well suited to apparatus that entail: high-pressure; pumping of solvent at relatively high flow-rates, such as 10s of milliliters per minute or greater; and/or mixing of solvents, such as methanol and water, that lead to significant reductions in gas solubility.

Accordingly, one embodiment of the invention features a method of liquid chromatography. The method includes providing one or more solvent reservoirs, providing a piston-based pump that includes at least one chamber, drawing one or more solvents into the pump in response to a pressure drop that promotes outgassing of the solvents, and dispersing outgassed bubbles into smaller bubbles to promote re-dissolution of the gas.

A second embodiment of the invention features a liquid-chromatography apparatus. The apparatus includes at least two solvent reservoirs, a gradient proportioning valve, a pump, at least one bubble-dispersing unit that receives a pressurized flow of proportioned solvents from the pump, and a control unit. The control unit includes a processor and a memory that stores instructions, which control proportioning of solvents to obtain a preselected solvent composition, and pumping at flow rates to support preparative-scale or process-scale liquid chromatography.

BRIEF DESCRIPTION OF THE DRAWING

The drawing is not necessarily to scale, emphasis instead generally being placed upon illustrating the principles of the invention.

DESCRIPTION

The phrase "isocratic-mode chromatography" herein refers to the use of a solvent composition that remains substantially constant as a function of time. During isocratic-mode chromatography, analytes in some samples elute while a fixed-concentration mobile phase flows through one or more columns.

The phrase "gradient-mode chromatography" herein refers to a flowing solvent composition that changes as a function of time, typically in response to a user-defined profile.

The term "preparative-scale liquid chromatography" herein refers to the use of liquid chromatography to isolate one or more compounds in a quantity and at a purity sufficient for further experiments or uses. Though preparative-scale liquid chromatography can refer to isolation of any quantity of a material (e.g., a few micrograms for a biochemist, or a few milligrams for an organic chemist,) the term "preparative-scale liquid chromatography" herein refers generally to methods and apparatus designed to isolate at least about 0.5 gram or more of a substance. Such methods and apparatus generally require relatively large solvent flow rates, e.g., at least about 5 ml/minute or more. In contrast, "analytical liquid chromatography" often entails flow rates of a few ml/minute or less.

Analytical liquid chromatography often uses a standard column inner diameter of 4.7 mm. Preparative-scale liquid chromatography, in contrast, typically uses columns having diameters of about 7.8 mm to about 100 mm, while "process-scale" (industrial) liquid chromatography typically uses columns of greater than 100 mm. Thus, for example, for pharmaceutical or biotechnological applications, a separation column can be as much as several feet in diameter to isolate kilograms of material.

Figure 1:
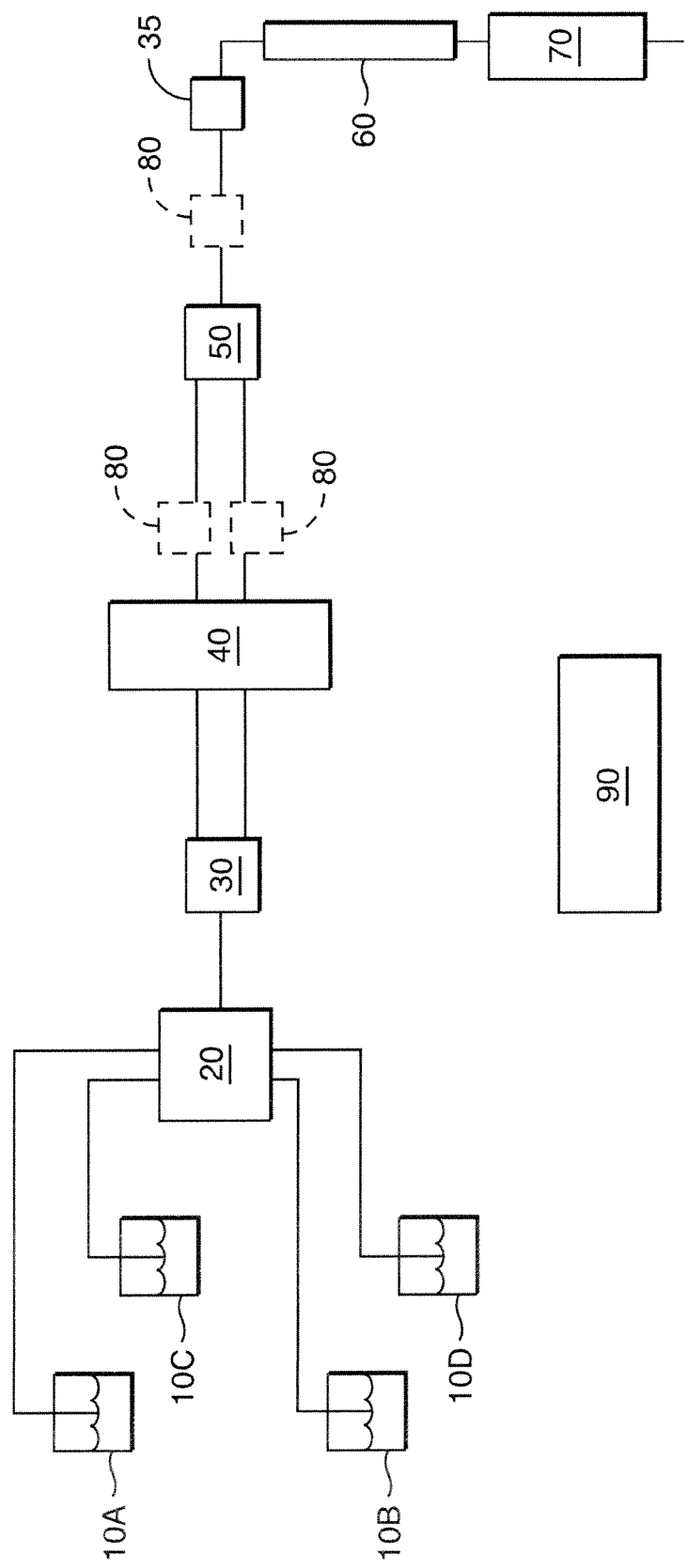
FIG. 1 is a block diagram of a liquid-chromatography apparatus, in accordance with one embodiment of the invention.

FIG. 1 is a block diagram of a liquid chromatography apparatus 100, suitable for preparative- or process-scale liquid chromatography, in accordance with one embodiment of the invention. The apparatus 100 includes four solvent reservoirs 10A, 10B, 10C, 10D, a gradient proportioning valve 20, an inlet manifold valve 30, a pump 40, a solvent mixer 50, one or more bubble-dispersing components 80 (shown in dashed outline at some optional locations,) an injector 35, a separation column 60, a detector 70, and a control unit 90.

In operation, the gradient proportioning valve 20 and the pump 40, in response to control of the control unit 90, select and draw one or more solvents from the reservoirs 10A, 10B, 10C, 10D. Any suitable gradient proportioning valve 20 is used, including commercially available valves. The valve 20 is operated, in response to control of the control unit 90, to provide a selected solvent composition, which is optionally varied in time, for example, to implement gradient-mode chromatography.

The bubble-dispersing component 80 is any component suitable for breaking up bubbles to reduce their size and thus enhance their re-dissolution. Suitable components include passive and active components. Some passive bubble-dispersing components are formed from a porous material having pore sizes much smaller than typical bubble sizes; upon traversing of the pumped solvent through the pores, the bubbles are dispersed, i.e., increased in number and reduced in size. The porosity, and thickness, of the material is preferably chosen to limit to an acceptable level the backpressure associated with the component 80.

Preferably, the bubble-dispersing component 80 is disposed as close as possible to a bubble source, to provide as much subsequent liquid pathway (and associated time) as possible for the dispersed bubbles to dissolve.

Returning to the subject of materials that are suitable for passive bubble fragmentation, some suitable porous material are particle- or mesh-based. A porous material is optionally produced by molding and/or sintering of particles; the particles optionally have fibrous, dentritic or spherical shapes, for example. The particles are, for example, metals, such as stainless steel, ceramic materials, such as alumina, glassy materials, or polymeric materials, such as polytetrafluoroethylene, or a combination of materials, or coated materials. Pore size is selectable in response to packing density, particle size and shape, particle composition, and processing conditions. Particles are joined by, for example, fusing or sintering. Fusing or sintering process conditions also affect the strength, pore size, and surface area of such porous materials.

In some implementations, the component 80 is formed from a thin material, such as mesh or a porous membrane; suitable membranes include an etched polycarbonate membrane, and a polymer such as a polyolefin, including polypropylene. A suitable mesh includes, for example, a stainless-steel screen. The screen or membrane is optionally coated, for example, with a fluorocarbon polymer. Some embodiments utilize a convention liquid-chromatography frit as a bubble-fragmenting component.

The solvent mixer 50 is any suitable mixer, including known passive and active mixers. In embodiments that generate bubbles in the mixer, a bubble-dispersing component 80 is preferably disposed downstream of the mixer 50. For example, one embodiment of the invention utilizes a water-solvent reservoir and a methanol-solvent reservoir. Upon mixing of water and methanol, the solubility of dissolved gas declines, thus often forcing bubbles to form and exit with the liquid exiting the mixer 50. In such a case, a bubble-dispersing component 80, as illustrated, is preferable disposed near to an exit port of the mixer 80.

The injector is any suitable injector 35, including known injectors, for injecting a sample into the solvent flow. The injector 35 is optionally disposed at alternative locations in the solvent flow path, as will be understood by one having ordinary skill in the liquid-chromatography arts.

The inlet manifold valve 30 is connected to an outlet tube from the gradient proportioning valve 20, and to two inlet tubes connected to the pump 40, to supply solvent to the two piston chambers. The inlet manifold valve 30 optionally includes a sample injector, to inject samples into the solvent prior to its entry into the pump 40.

The control unit 90—including, for example, a personal computer or workstation—receives data and/or provides control signals via wired and/or wireless communications to, for example, the gradient-proportioning valve 20, the pump inlet manifold 30, the pump 40, and/or the detector 70. The control unit 90 supports, for example, automation of sample processing. The control unit 90, in various illustrative embodiments, is implemented in software, firmware, and/or hardware (e.g., as an application-specific integrated circuit). The control unit 90 includes and/or is in communication with storage component(s).

Suitable implantations of the control unit 90 include, for example, one or more integrated circuits, such as microprocessors. A single integrated circuit or microprocessor in some alternative embodiments includes the control unit 90 and other electronic portions of the apparatus 100. In some embodiments, one or more microprocessors implement software that enables the functions of the control unit 90. In some embodiments, the software is designed to run on general-purpose equipment and/or specialized processors dedicated to the functionality herein described.

In some implementations of the apparatus 100, the control unit 90 includes a user interface to support interaction with the control unit 90 and/or other portions of the apparatus 100. For example, the interface is configured to accept control information from a user and to provide information to a user about the apparatus 100. The user interface is used, for example, to set system control parameters and/or to provide diagnostic and troubleshooting information to the user. In one embodiment, the user interface provides networked communication between the apparatus 100 and users located either local to the operating environment or remote from the operating environment. The user interface in some implementations is used to modify and update software.

In view of the description of illustrative embodiments provided herein, it will be apparent to one having ordinary skill in the separation arts that various other configurations and implementations of control units can be utilized in other embodiments of the invention to provide automated control of process-scale and preparative-scale chromatography.

The pump 40 is configured to provide solvent at pressures of at least 500 psi, or 1,000 psi, or 5,000, psi 10,000 psi or greater. The pump includes any suitable piston-based pump, including known pumps, such as available from Waters Corporation, Milford, Mass.

The column 60 is any column suitable for process-scale and preparative-scale chromatography. The column contains, for example, any medium suitable for such a purpose, including known media. The sorbent material is selected from any suitable sorbent material, including known materials such as silica or a mixture of silica and a copolymer such as an alkyl compound. The solvents are any solvents suitable to a desired separation process, including known solvents.

Figure 2:
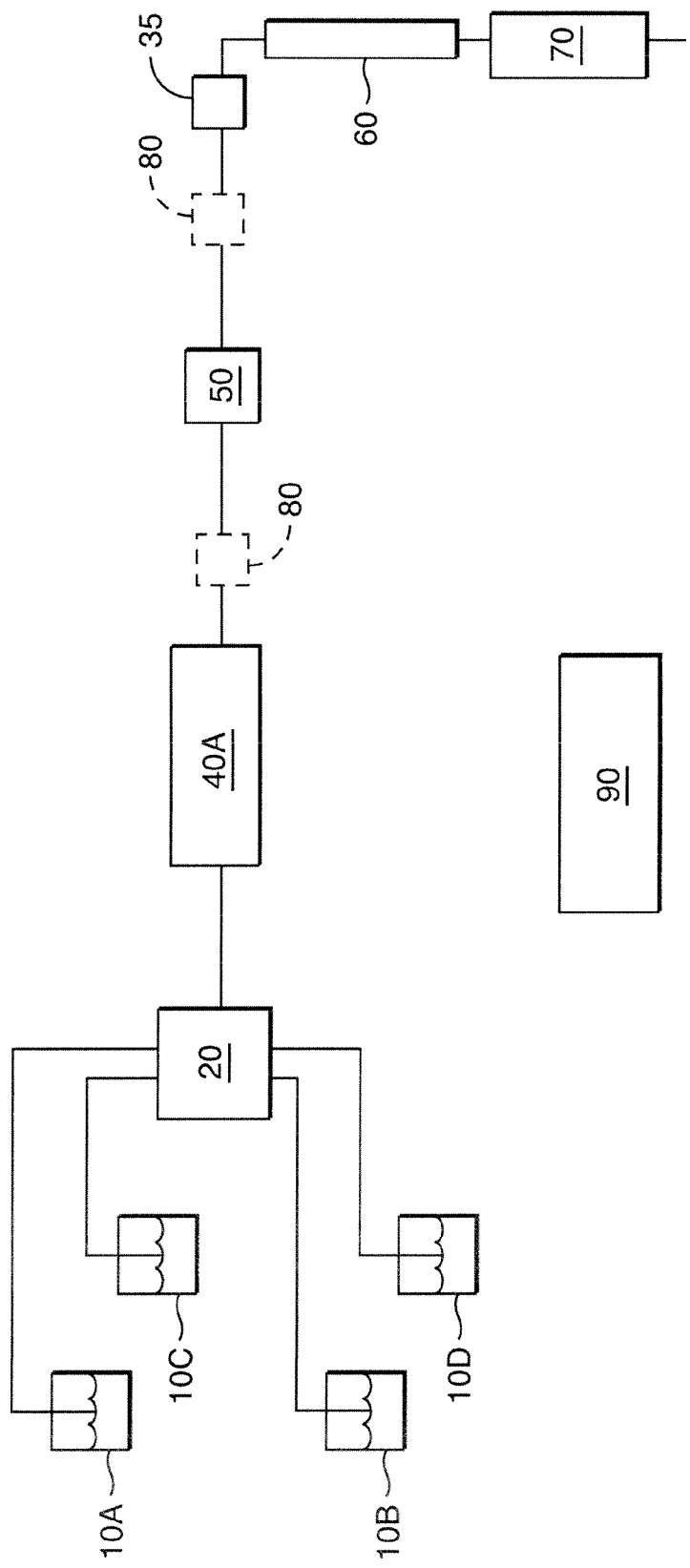
FIG. 2 is a block diagram of a liquid-chromatography apparatus, in accordance with one embodiment of the invention.

FIG. 2 is a block diagram of a liquid chromatography apparatus 200, in accordance with another embodiment of the invention. The apparatus 200 largely includes components similar to that of the apparatus 100 illustrated in FIG. 1, as identified by the common reference characters.

The apparatus 200 has a pump 40A, however, that includes two serially disposed piston chambers, in contrast to the parallel use of piston chambers found in the pump 40 of the apparatus 100. In this embodiment, the outlet tube from the gradient proportioning valve 20 is connected to one of the chambers of the pump 40A. Other embodiments of the invention utilize pumps having a single piston chamber or multiple piston chambers in serial and/or parallel configurations. More generally, principles of the invention are applicable to pumping systems that subject a fluid, such as a solvent, to a reduction in pressure, sufficient to cause outgassing of dissolved gasses.

Variations, modifications, and other implementations of what is described herein will occur to those of ordinary skill in the art without departing from the spirit and the scope of the invention as described. For example, In view of the above description, it will be apparent that the number and/or arrangement of various components of the above-described apparatus 100 are optionally modified, while still exploiting the disclosed solution to bubble formation. For example, alternative embodiments of the invention include more than one column, fewer or greater than four solvents, fewer or greater than two piston chambers, and one or more bubble dispersing units at various alternative locations down stream of bubble sources. Accordingly, the invention is to be defined not by the preceding illustrative description but instead by the scope of the following claims.

What is claimed is:

1. A liquid-chromatography apparatus, comprising:
   at least two solvent reservoirs respectively containing a first solvent and a second solvent, which each contain dissolved gas;
   a gradient proportioning valve in fluid communication with the at least two solvent reservoirs;
   a pump comprising at least two pistons disposed in respective chambers in parallel or serial fluid communication with an outlet of the gradient proportioning valve to receive a flow of proportioned solvents from the gradient proportioning valve;
   at least one bubble-dispersing unit in fluid communication with the pump to receive a pressurized flow of proportioned solvents from the pump and to disperse bubbles in the flow; and
   a control unit, in communication with the pump and the gradient proportioning valve, and comprising at least one processor and at least one memory for storing a plurality of instructions, which, when executed by the at least one processor, causes implementation of the steps of,
   repeatedly switching the gradient proportioning valve to provide the proportioned solvents in association with a preselected solvent composition, and
   drawing the selected solvent mixture into the pump at a flow rate of at least 5 ml/min.

2. The apparatus of claim 1, wherein the at least one bubble-dispersing component is disposed at an output port of the pump.

3. The apparatus of claim 1, further comprising a solvent mixer in fluid communication with the pump to receive the pressurized flow of proportioned solvents from the pump, wherein the at least one bubble-dispersing component is disposed in a flow path closer to an outlet port of the mixer than to an inlet port of a separation column.

4. The apparatus of claim 3, wherein the at least one bubble-dispersing component is disposed at the output port of the mixer.

5. The apparatus of claim 1, wherein the first solvent comprises water and the second solvent comprises methanol.

6. The apparatus of claim 1, wherein the apparatus does not include a vacuum degasser.

7. The apparatus of claim 1, wherein each of the chambers have a chamber volume in a range of 0.5 ml to 2 ml.

8. The apparatus of claim 1, wherein the bubble-dispersing component comprises a mesh or a porous material.

9. The apparatus of claim 1, wherein the plurality of instructions further cause implementation of the step of providing the pressurized flow of proportioned solvents from the pump at a pressure of at least 500 pounds per square inch.

10. The apparatus of claim 1, further comprising an injector for injecting a sample into the flow of proportioned solvents, wherein the bubble-dispersing unit is disposed upstream of the injector.

11. The apparatus of claim 10, wherein the at least one bubble-dispersing component is disposed at an output port of the pump.

12. The apparatus of claim 10, further comprising a solvent mixer in fluid communication with the pump to receive the pressurized flow of proportioned solvents from the pump, wherein the at least one bubble-dispersing component is disposed in a flow path closer to an outlet port of the mixer than to an inlet port of a separation column.

* * * * *